US005549602A

United States Patent [19]

Farkas

[11] Patent Number: 5,549,602
[45] Date of Patent: Aug. 27, 1996

[54] ENDOSCOPIC LASER THERAPY PLUME AND EFFLUENT COLLECTION DEVICE

[76] Inventor: Paul S. Farkas, 21 Erskine Dr., Longmeadow, Mass. 01106

[21] Appl. No.: 467,225

[22] Filed: Jun. 6, 1995

Related U.S. Application Data

[63] Continuation-in-part of Ser. No. 273,393, Jul. 11, 1994, abandoned.

[51] Int. Cl.⁶ ............................ A61M 1/00; A61M 31/00
[52] U.S. Cl. .................. 606/15; 606/10; 604/35; 604/48; 604/319
[58] Field of Search ................... 604/317–319, 604/35, 48, 20; 606/10, 14; 128/4, 6, 7, 14, 16; 600/108, 156

[56] References Cited

U.S. PATENT DOCUMENTS

| 3,982,541 | 9/1976 | L'Esperance, Jr. ......................... 606/3 |
| 4,122,853 | 10/1978 | Smith . |
| 4,580,556 | 4/1986 | Kondur ........................ 128/6 |
| 4,648,386 | 3/1987 | Morritt et al. . |
| 4,735,603 | 4/1988 | Goodson et al. . |
| 4,850,352 | 7/1989 | Johnson . |
| 4,863,447 | 8/1989 | Smith ...................... 604/335 |
| 5,154,709 | 10/1992 | Johnson . |
| 5,186,714 | 2/1993 | Boudreault et al. . |
| 5,199,944 | 4/1993 | Cosmescu . |
| 5,209,219 | 5/1993 | Hollobaugh ................. 128/6 |
| 5,257,773 | 11/1993 | Yoshimoto et al. ................. 128/4 |
| 5,267,996 | 12/1993 | Fletcher . |
| 5,324,254 | 6/1994 | Phillips ..................... 606/14 |
| 5,336,169 | 8/1994 | Divilio et al. ........... 604/319 |

FOREIGN PATENT DOCUMENTS

| 2562424 | 4/1984 | France . |
| 595897 | 4/1993 | Japan . |

Primary Examiner—Mary Beth Jones
Assistant Examiner—Dennis Ruhl
Attorney, Agent, or Firm—Fishman, Dionne & Cantor

[57] ABSTRACT

A plume and effluent collection device is disclosed for use with an endoscopic laser therapy device which is adapted to engage a biopsy port in a laser device. The collection device, is also engageable with a remote vacuum system, so that any plume or effluent from within a patient's body which migrates to the exterior through the biopsy port on the laser device, will be safely contained and removed from the operating environment. The device enhances the safety of Doctors and technicians using laser therapy devices.

17 Claims, 2 Drawing Sheets

ENDOSCOPIC LASER THERAPY PLUME AND EFFLUENT COLLECTION DEVICE

CROSS-REFERENCE TO RELATED APPLICATION:

This is a continuation-in-part application of U.S. patent application Ser. No. 08/273,393 filed Jul. 11, 1994, now abandoned.

BACKGROUND OF THE INVENTION

1. Field of the Invention

The invention relates to the field of endoscopic laser therapy and a device adapted to minimize health risks associated with plume or bodily fluid leakage from a biopsy port in an endoscope used for laser therapy.

2. Prior Art

Endoscopic laser surgery is continuing to grow in developed countries world wide; this growth is in both popularity and indications. As popularity and familiarity with laser processes grow there is increasing concern over the "plume" or smoke associated with laser vaporization or cauterization and with the leakage of bodily fluids. Generally, physicians and technicians are concerned with the plume or fluids remaining trapped in the body cavity and inhibiting the effectiveness of the surgery by obscuring either the objects of the laser surgery or the laser itself. Therefore, many devices have been described and or patented which remove the plume or fluids from the body cavity of a patient. These devices include suction means and various other apparati to be used therewith such as vaporizers, flushing fluid, etc. However, no publication addresses the problem of the plume or bodily fluid exiting the end biopsy port of the endoscope used in laser therapy.

As is understood by one skilled in the art, the escape of smoke or bodily fluids through the biopsy port is a health risk to physicians or technicians because the port is located proximately to these individuals. The breathing in of smoke and small particulate matter or contacting of fluids is a serious health hazard, especially when the patient being attended to is carrying any of the highly infectious diseases prevalent today. Some of the diseases about which concern is harbored are AIDS, HEPATITIS; etc. Although the risk is significant it has not previously been addressed.

SUMMARY OF THE INVENTION

The above-discussed and other drawbacks and deficiencies of the prior art are overcome or alleviated by the aspiration device of the present invention.

The present invention solves the problem of escaping plume and fluids through the biopsy port of an endoscopic laser therapy device by providing a device for engagement with the biopsy port which functions to capture and dispose of escaping plume and bodily fluids. The invention comprises a hollow structure wherein one end is sealed and an opposite end is adapted to be connected to a suction device to collect and dispose of fluids escaping from the biopsy port. The hollow structure usually contains one aperture appropriately sized to fit over a biopsy port; one opening to accept forceps when necessary and one adaption to engage a suction apparatus. Upon the application of suction to the aspiration device, when properly engaged with a biopsy port, plume and bodily fluids emanating from the biopsy port are immediately removed to a disposal area. The operator of the equipment is therefore not subject to such plume or other fluids and risk for these operators is reduced.

The above-discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several FIGURES:

FIG. 4 is an elevational view of the invention illustrating an access opening for accessing the biopsy port with forceps or the like.

DESCRIPTION OF THE PREFERRED EMBODIMENT

The invention is highly suited to minimize the risk of contracting a contagious disease by either inhaling the aerosol associated with the cauterizing action of an endoscopic laser or by contacting other bodily fluids expressed during surgery and which are conducted along the laser housing to the point of the biopsy port where such fluids escape. Risk in these circumstances is managed by preventing escape of the noted fluids into the ambient atmosphere through the biopsy port of the laser device.

Figure 1:
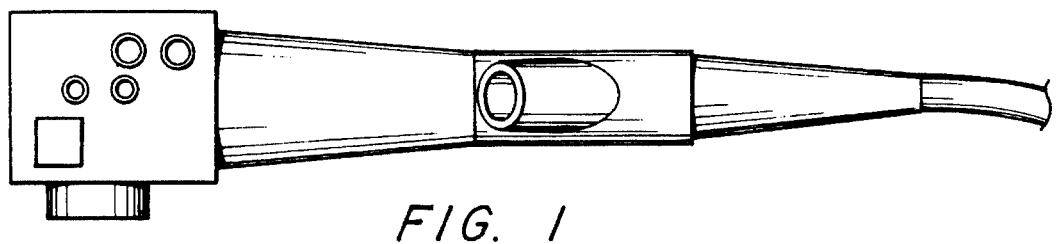
FIG. 1 is a conventional endoscopic laser illustrating the location of the biopsy port.
Figure 2:
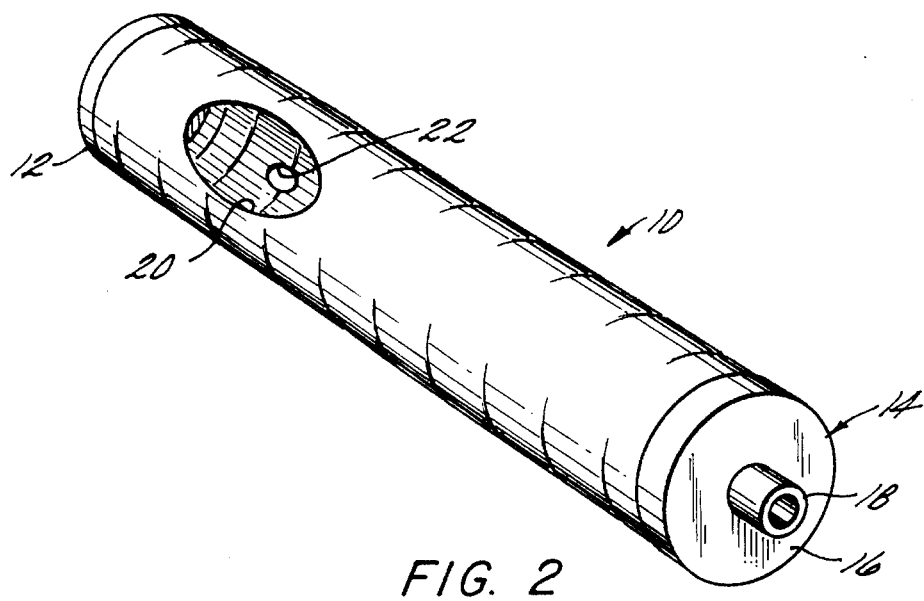
FIG. 2 is a perspective view of the aspiration device of the invention.

For the sake of clarity FIG. 1 is included to illustrate a conventional art endoscope and biopsy port to which this invention is directed.

The invention comprises a hollow structure of a predetermined length, which is preferably transparent. The structure is most preferably cylindrical and is illustrated as such in drawings 2, 3 and 4 by numeral 10. The cylinder is most preferably in the range of about 5.08 centimeters (2 inches) to about 12.7 centimeters (5 inches) in length and is about 2–3 centimeters in diameter. It will be understood, however, that the length of the hollow structure can be any length the doctor or technician desires. The diameter of the cylinder is limited only by practicality.

In the most preferred embodiment the cylinder includes a sealed end 12 and a suction engagement arrangement 14 on the other end. Sealed end 12 may be a cover, tape, fused, etc.; any method by which the open end of the hollow structure may be closed is acceptable and within the scope of the invention. The suction engagement arrangement 14 generally comprises an end cap 16 adapted to be engaged with the cylindrical hollow structure 10, said end cap 16 having a nipple 18 extending therefrom for engagement with a conventional suction device (not shown). The end cap 16 may be fastened to cylinder 10 by conventional means, for example, screw threads, glue, tape, etc. It should be noted that other engagement arrangements for engaging the suction apparatus to the aspiration device, such as a taper used in place of the nipple, threads provided on the nipple or on the taper etc., are perfectly suitable to the invention.

Figure 3:
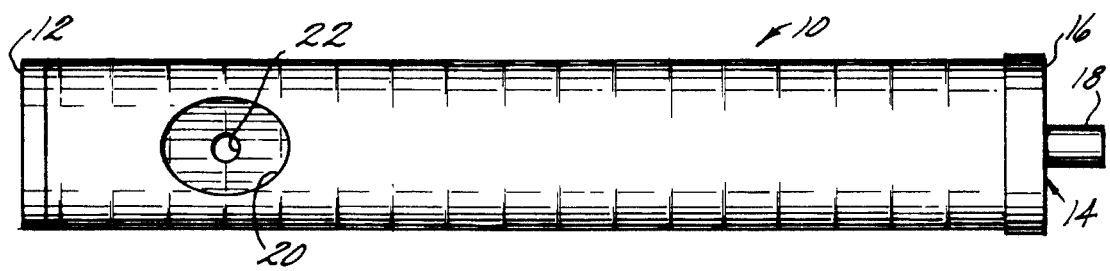
FIG. 3 is an elevational view of FIG. 2 illustrating an aperture for engagement with a biopsy port.
Figure 4:
Figure 5:
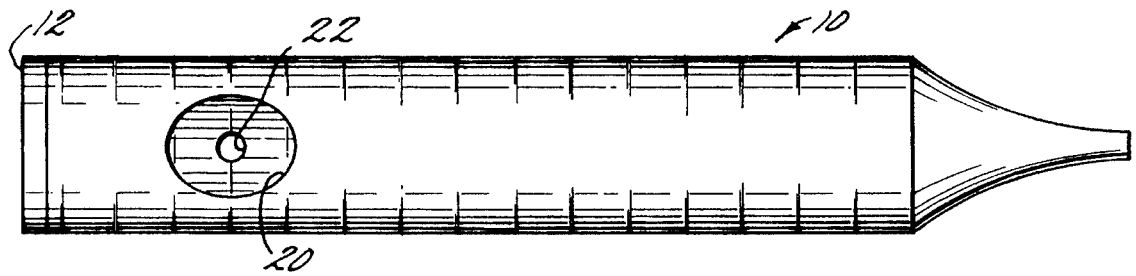
FIG. 5 is an elevational view of the aspiration device with a nipple for slip fit engagement with a suction device.
Figure 6:
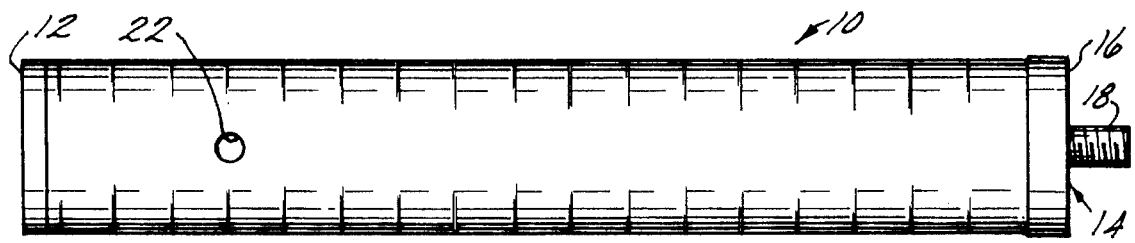
FIG. 6 is an elevational view of the aspiration device with a threaded engagement for connection to a suction device.
Figure 7:
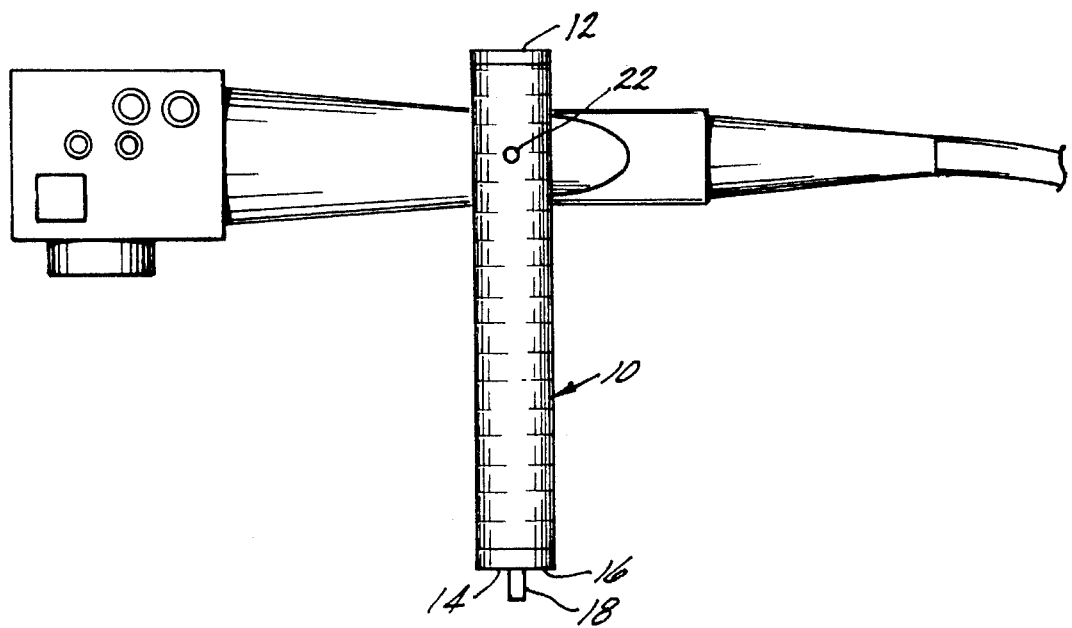
FIG. 7 is a view showing the aspiration device connected to the endoscopic laser device.

Referring now to FIGS. 3 and 4, the aspiration device of the invention includes a biopsy port aperture 20 for engaging the biopsy port of an endoscopic laser therapy device. Generally, the aperture 20 is dimensioned so that a biopsy port of a conventional endoscopic laser device will be completely covered by said aperture. It should be noted however that other types of engagement arrangements are within the scope of the invention with the sole caveat that the engagement must be sufficient to allow the aspiration device and suction line to effectively entrap and transport to disposal facilities, fluids escaping from the biopsy port. In the preferred embodiment, the aperture is in the range of about 0.5 to about 2 inches in diameter, within this range the most preferred aperture size is about 1.5 inches in diameter.

A forceps opening 22 is provided so that the physician or technician utilizing the device is provided with access to the biopsy port. This is important since many procedures include the use of forceps or similar instruments in conjunction with the laser. It is therefore desirable to provide such access through the aspiration device so as not to forsake safety considerations while such forceps or similar instruments are being utilized. Most preferably the opening 22 is much smaller than the biopsy port aperture 20 so that even when no instrument is being used, fluids escaping from the patient will not emanate through the opening 22. The most preferred range for forceps opening size is about 1 millimeter to about 4 millimeters in diameter; within this range the most preferred opening size is about 2 millimeters in diameter. General principles of physics explain this occurrence in that the lower pressure created by the suction device, inside the hollow structure necessarily draws air in through the forceps opening and therefore fluids will not be easily able to move against the air flow direction.

The biopsy port aperture 20 and forceps opening 22 can be positioned from about 170° to about 190° of each other measured circumferentially about the preferred cylindrical hollow structure.

Flexibility in the aspiration device is desirable but not essential.

It is contemplated that the device may be secured to the housing of a conventional endoscopic laser therapy device using any conventional engagement means including, but not limited to, tape, glue, welding, hook and loop fasteners, slip fit engagement, threaded engagement means and slotted engagement means.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. An aspiration device in combination with an endoscopic laser device comprising a hollow structure, sealed at one end and adapted to be engaged with a suction apparatus at the other end, said structure including and defining at least two apertures, said apertures being a biopsy port opening in communicative engagement with a biopsy port on the endoscopic laser device and a forceps opening located on the hollow structure from about 170° to about 190° circumferentially from said biopsy port such that a forceps is easily insertable through said forceps opening and into said biopsy port, whereby said aspiration device entraps and said suction apparatus is capable of disposing of effluent materials emanating from the biopsy port.

2. An aspiration device as claimed in claim 1 wherein said hollow structure is at least two inches in length.

3. An aspiration device as claimed in claim 1 wherein said hollow structure is about two to five inches in length.

4. An aspiration device as claimed in claim 1 wherein said hollow structure is about three inches in length.

5. An aspiration device as claimed in claim 1 wherein said hollow structure is tubular.

6. An aspiration device as claimed in claim 1 wherein said hollow structure is transparent tubing.

7. An aspiration device as claimed in claim 1 wherein the end adapted to be engaged with a suction apparatus includes a nipple for slip fit engagement with a suction tube.

8. An aspiration device as claimed in claim 1 wherein the end adapted to be engaged with a suction apparatus includes a taper in the hollow structure such that a suction tube is engageable therewith.

9. An aspiration device as claimed in claim 1 wherein said end adapted to be engaged with a suction apparatus includes a threaded portion whereby said hollow structure is engageable by screwing the suction apparatus and hollow structure together, said threaded portion having threads complimentary to a threaded arrangement in said suction apparatus.

10. An aspiration device as claimed in claim 1 wherein the biospy port opening is in the range of about 0.5 to two inches in diameter.

11. An aspiration device as claimed in claim 1 wherein the biospy port opening is in the range of about 1.5 inches in diameter.

12. An aspiration device as claimed in claim 1 wherein said forceps opening is smaller in diameter than said biopsy port opening.

13. An aspiration device as claimed in claim 1 wherein said forceps opening is in the range of about 1 mm to about 4 mm in diameter.

14. An aspiration device as claimed in claim 1 wherein said forceps opening is about 2 mm in diameter.

15. An aspiration device as claimed in claim 1 wherein the biopsy port opening is engageable with the biopsy port by conventional fastening means.

16. An aspiration device as claimed in claim 15 wherein said fastening means is selected from the group consisting of tape, glue, welding, hook and loop fastener, slip fit engagement means, threaded engagement means and slotted engagement means.

17. An aspiration device as claimed in claim 1 wherein said hollow structure is flexible.

\* \* \* \* \*